United States Patent [19]
Dadey

[11] Patent Number: 5,935,599
[45] Date of Patent: Aug. 10, 1999

US005935599A

[54] POLYMER-ASSOCIATED LIPOSOMES FOR DRUG DELIVERY AND METHOD OF MANUFACTURING THE SAME

[75] Inventor: Eric J. Dadey, Aurora, Ill.

[73] Assignee: The Board of Trustees of the University of Illinois, Urbana, Ill.

[21] Appl. No.: 08/958,280

[22] Filed: Oct. 27, 1997

Related U.S. Application Data

[60] Provisional application No. 60/029,039, Oct. 28, 1996.
[51] Int. Cl.$^6$ ................................................ A61K 9/127
[52] U.S. Cl. ..................... 424/450; 424/1.21; 424/9.321; 424/9.51; 424/417; 428/402.2; 264/4.1
[58] Field of Search ................... 424/450, 9.321, 424/9.51, 417; 428/402.2; 264/4.1, 1.21

[56] References Cited

U.S. PATENT DOCUMENTS

| | | | |
|---|---|---|---|
| 3,577,534 | 5/1971 | Koh et al. | 424/183 |
| 4,489,065 | 12/1984 | Walton et al. | 424/180 |
| 4,834,965 | 5/1989 | Martani et al. | 424/488 |
| 5,008,109 | 4/1991 | Tin | 424/422 |
| 5,443,505 | 8/1995 | Wong et al. | 623/4 |
| 5,478,575 | 12/1995 | Miyazaki et al. | 424/487 |

FOREIGN PATENT DOCUMENTS

| | | | |
|---|---|---|---|
| 0 424 168 | 4/1991 | European Pat. Off. | A61K 47/32 |
| 862242 | 3/1961 | United Kingdom . | |

OTHER PUBLICATIONS

Lindahl et al., *Ann. Rev. Biochem.*, 47, 00. 385–417, 1978.
Kjellen et al., *Biochem. Biophys. Res. Commun.*, 74(1), pp. 126–133, 1977.
Hiebert et al., *Thrombosis Res.*, 8, pp. 195–204, 1976.
Barzu et al., *Nouv. Rev. Fr. Hematol.*, 26, pp. 243–247, 1984.
Barzu et al., *J. Med. Chem.*, 36, pp. 3546–3555, 1993.
Baba et al., *Antimicrobioal. Agents and Chemotheraphy*, 34(1), pp. 134–138, 1990.
Tsuchida et al., Interactions Between Macromolecules in Solution and Intermacromolecular Complexes in Advances in Polymer Science, vol. 45, Germany, 1982.
Garmbaro et al., *Kidney Int.*, 42, pp. 285–291, 1992.
Gambaro et al., *Kidney Int.*, 46, pp. 797–806, 1994.
Marano et al., *Invest. Opthalmology Vis. Sci.*, 33(9), pp. 2619–2625, 1992.
Templeton, *Lab. Invest.*, 61(2), pp. 202–211, 1989.
Gambaro et al., *Metabolism*, 38(5), pp. 419–420, 1989.
Deckert et al., *Diabetes*, 40, pp. 764–770, 1991.
Olczyk et al., *Acta Biochimica Polonica*, 39, pp. 101–105 1992.
Brange, Stability of Insulin, Kluwer Academic Publishers, Lancaster, England, pp. 75–103, 1994.
Obrink et al, *Biochem. J.* , 121, pp. 227–233, 1971.
Gelman et al., *Biochimica et Biophysica Acta*, 342, pp. 254–261, 1974.
Burstein et al., *J. Lipid Res.*, 11, pp. 583–595, 1970.
Gelman et al., *Biochimica et Biophysica Acta*, 297, pp. 452–455, 1973.
Villanueva et al., *Biochem. and Biophys. Res. Commun.*, 74(2), pp. 803–809. 1977.
Patel et al., *Bioscience Reports*, 3, pp. 39–46, 1983.
Encyclopedia of Pharmaceutical Technology, vol. 9, Marcel Dekker, Inc., NY, NY, Swarbrick, Ed., pp. 1–39, undated.
Scott, *Methods of Biomedical Analysis*, vol. VIII, pp. 145–197, undated.
Zalipsy. FEBS Letters 353, pp. 71–74 (1994).

*Primary Examiner*—Gollamudi S. Kishore
*Attorney, Agent, or Firm*—Marshall, O'Toole, Gerstein, Murray & Borun

[57] ABSTRACT

Novel polymer-associated liposomes (PALs) containing a liposome, and a polymer having a plurality of acid moieties, like sulfonic acid moieties, carboxyl moieties, or phosphonic acid moieties, in a salt form are disclosed. Drug compositions containing a PAL and a drug are administered to individuals suffering from a disease, and the drug is released, in vivo, to treat the disease, and to reduce, eliminate, or reverse complications associated with the disease.

26 Claims, 4 Drawing Sheets

POLYMER-ASSOCIATED LIPOSOMES FOR DRUG DELIVERY AND METHOD OF MANUFACTURING THE SAME

CROSS-REFERENCE TO RELATED APPLICATIONS

This application claims the benefit of provisional application Ser. No. 60/029,039, filed Oct. 28, 1996.

FIELD OF THE INVENTION

The present invention relates to polymer-associated liposomes (PALs) and their method of preparation, to drug compositions containing a PAL and a drug, and to the administration of the drug compositions to individuals. More particularly, the present invention relates to a new drug delivery system comprising a PAL, wherein the PAL contains a liposome that is noncovalently bound, i.e., is complexed, to an anionic polymer having a plurality of acid moieties in a salt form. A PAL is prepared by interacting the anionic polymer and a liposome, in an aqueous medium, to form a liposome/polymer complex, isolating the complex in water from an organic solvent, and rehydrating the complex to form the PAL. The PAL can be incorporated into a variety of drug compositions, including liquid and solid phase drug composition, for administration of a therapeutic agent orally or by injection.

BACKGROUND OF THE INVENTION

It is well known that modern day drugs are very efficacious with respect to treating acute and chronic diseases. However, several diseases, and especially chronic diseases, are associated with complications that are not treated by administration of the drug.

For example, the standard treatment for diabetes is administration of insulin. An individual suffering from diabetes does not produce sufficient insulin, and hence the individual cannot burn and store glucose. Diabetes cannot be cured, but diabetes can be treated by periodic injections of insulin. FIG. 1 shows that serum insulin levels rise from a low fasting value to a peak after about 30 to 60 minutes, then fall back to a low value after about 120 minutes. In mild diabetics, the rise in serum insulin is lower compared to normal individuals. In severe diabetics, no insulin is produced, and the rise in serum insulin levels is negligible. As a result, excess glucose accumulates in the blood of a diabetic, which can result, for example, in a loss of weight and loss of strength.

However, insulin injections to treat diabetes do not treat, or alleviate, the serious vascular complications associated with diabetes, including nephropathy, retinopathy, neuropathy, heart disease, and reduced blood circulation in the limbs, i.e., "diabetic foot," that can lead to gangrene. Another disadvantage with respect to the present therapeutic compositions used to treat diabetes is that insulin must be injected. Insulin cannot be administered orally because insulin is destroyed by the strong acid conditions of the stomach.

Therefore, it would be advantageous to develop a method of both treating a disease, and preventing or reversing complications associated with the disease. It also would be advantageous to develop easier methods of administering a drug to treat the disease. As set forth in detail hereafter, the present invention is directed to novel PALs, and to drug compositions containing a PAL and a therapeutic agent, i.e., a drug, to reduce, eliminate, or reverse complications associated with a disease. The present invention is further directed to a method of manufacturing a PAL, and to improved drug delivery systems for administering difficult to administer drugs, like insulin.

With respect to diabetes, glycosaminoglycans (GAGs) are a class of negatively charged, endogenous polysaccharides composed of repeating sugar residues (uranic acids and hexosamines). GAGs have been shown to bind a variety of biological macromolecules, including connective tissue macromolecules, plasma proteins, lysosomal enzymes, and lipoproteins. In addition, exogenous GAGs have been shown to bind to the cell surfaces of a variety of different cell types, including liver cells (hepatocytes), fibroblasts, and importantly, endothelial cells. Exogenous GAGs therefore can be internalized. Furthermore, GAGs have been implicated in the regulation of cell proliferation and in cell-cell communication, shown to interact with cell-surface receptors (cell adhesion molecules), and shown to modify the behavior of cells in culture. In addition, GAGs were shown to be highly potent, selective inhibitors of HIV replication and giant cell formation. These findings suggest that exogenously administered GAGs have the potential to target a variety of important in vivo sites.

GAG-receptor interactions are characterized by the formation of noncolavent, self-assembling macromolecular complexes. These transient, interpoly-electrolyte complexes mediate many biological functions including enzyme-substrate binding, antigen-antibody interactions, leukocyte-endothelial cell adhesion events, drug-receptor binding, and protein—protein interactions. Furthermore, secondary binding forces, such as hydrogen bonds, vander Waals forces, and hydrophobic interactions, govern interpoly-electrolyte formation, and, ultimately, influence the resulting pharmacologic response to the complex.

G. Gambaro et al., *Kidney Int.*, 46, pages 797–806 (1994) discloses that exogenously administered GAGs have a favorable effect on morphological and functional renal abnormalities in diabetic rats, and appear to revert established diabetic renal lesions. Furthermore, D. M. Templeton, *Lab. Invest.*, 61 (2), pages 202–211 (1989) and C. W. Marano et al., *Invest. Ophthalmology Vis. Sci.*, 33 (9), pages 2619–2625 (1992) disclose that diabetic patients have a decreased glycosaminoglycan content in glomerular basement membranes. Additionally, an increase in total GAG serum levels in diabetic patients was disclosed in K. Olczyk et al., *Acta Biochimica Polonica*, 39, pages 101–105 (199). The authors observed an increase in protein-bound GAGs, such as keratan sulfate, hyaluronic acid, heparin sulfate, and heparin in diabetic patients. Gambaro et al. also discloses an increase in the urinary excretion rate of GAGs from insulin-dependent diabetic patients.

Therefore, publications show that glycosaminoglycans play an important, yet unexplained, role in the vascular changes associated with lifelong insulin therapy. In particular, administration of GAGs to diabetic animals has inhibited or reversed some vascular abnormalities. The publications also strongly suggest that exogenous insulin plays a role in elevating the level of GAGs in the urine and serum of diabetic patients. Furthermore, the publications clearly show that glycosaminoglycans bind to a multitude of biological macromolecules, including proteins.

These observations appear to suggest utilizing glycosaminoglycans as an adjuvant to insulin therapy. However, GAGs are anticoagulants and long term use of GAGs with insulin would thin the blood of an individual to unacceptable levels. Furthermore, the risks associated with a long term use of GAGs are unknown. In addition, GAGs are heterogeneous, having a relatively wide molecular weight range of about 8,000 to about 20,000, and accordingly are difficult to reproduce. Therefore, although persons skilled in the art have used GAGs as therapeutic agents, e.g., heparin, GAGs have not been used for extended periods of time, or for the treatment of a chronic disease, like diabetes. The present invention is directed to finding drug delivery systems that provide the benefits of a drug-GAGs complex, but that avoid the disadvantages associated with long term administration of a GAG compound.

SUMMARY OF THE INVENTION

The present invention is directed to a novel drug delivery system, wherein a liposome is complexed, noncovalently, with an anionic polymer having a plurality of acid moieties in a salt form to form a PAL. A PAL is formulated with a drug or a therapeutic agent to provide a drug composition that treats an underlying disease, e.g., insulin to treat diabetes, and also treats complications associated with the disease, e.g., prevent or reverse the vascular problems associated with diabetes. The present PALs can be formulated with either water-soluble or water-insoluble drugs, or both. Therefore, a drug composition containing a PAL and a drug can be administered in a variety of dosage forms. Furthermore, because different anionic polymers have an affinity for different specific cell surfaces, site-specific drug delivery can be achieved by a proper selection of the anionic polymer of the PAL.

More particularly, the present invention is directed to a polymer-associated liposome (PAL) containing a liposome and an anionic polymer having: (a) a plurality of acid moieties in a salt form, and (b) a weight average molecular weight ($M_w$) of about 1,000 to about 1,000,000. The liposome comprises a phospholipid, like lecithin, for example.

In accordance with an important aspect of the present invention, the PAL contains a liposome that is electrostatically bound to, or complexed with, the anionic polymer, as opposed to forming a covalent bond between the liposome and anionic polymer. The anionic polymer contains a plurality of acid moieties, in the salt form, to achieve complexation with the liposome. The free acid moiety of the polymer can be a carboxyl group, sulfate group, sulfonate group, phosphonic acid group, phosphoric acid group, phenolic group, or a similar acid moiety. In the preparation of a PAL, the acid moieties of the anionic polymer are present predominantly in the anionic, or salt, form, as opposed to the free acid form. Preferred drugs used in a drug composition containing a PAL are polypeptides, genes, or proteins.

Therefore, one aspect of the present invention is to provide a PAL wherein the anionic polymer is a naturally occurring polymer or a synthetic polymer.

Another aspect of the present invention is to provide a PAL containing a liposome and an anionic polymer in a weight ratio of liposome to anionic polymer of about 80 to about 20 to about 95 to about 5.

Yet another aspect of the present invention is to provide a drug composition containing a drug and PAL, wherein the composition can be administered to an individual in a liquid form either orally or by injection.

Still another aspect of the present invention is to provide a drug composition containing a drug and a PAL in a lyophilized form, such that the drug can be administered to an individual in a solid form. Such a solid composition is especially useful for the oral administration of a drug to an individual.

Another aspect of the present invention is to provide a drug composition containing a drug, i.e., a therapeutic agent, and a PAL that can be administered to an individual to treat an acute or chronic disease and to alleviate, eliminate, or reverse complications associated with the disease. In preferred embodiments, the drug is a gene, insulin, methotrexate, isoniazid, chloroquine phosphate, a polypeptide, or a protein.

Another aspect of the present invention is to provide PALs that remain intact and do not dissociate in the vascular system shortly after administration, and that are capable of releasing the drug over time in vivo to treat a disease. Yet another aspect of the present invention is to provide a drug composition containing a drug and a PAL that is site specific for improved delivery of the drug and improved treatment of the disease of concern.

Another aspect of the present invention is to provide a PAL containing liposome comprising a phospholipid having a quaternary ammonium nitrogen atom, and a salt form of a polymer selected from the group consisting of polyvinylsulfonic acid, polyacrylic acid, polyvinylphosphonic acid, and mixtures thereof.

Yet another aspect of the present invention is to provide a drug composition containing insulin and a PAL that treats diabetes and that prevents, alleviates, or reverses vascular complications that are associated with diabetes and that are left unchecked by conventional insulin formulations.

One other aspect of the present invention is to provide alternate routes of administration for the safe, easy, and effective delivery of a drug to a specific target site, especially to provide an oral route of administration for the drug.

These and other novel features and aspects of the present invention will become apparent from the following detailed description of the preferred embodiments.

DETAILED DESCRIPTION OF THE PREFERRED EMBODIMENTS

Figure 1:
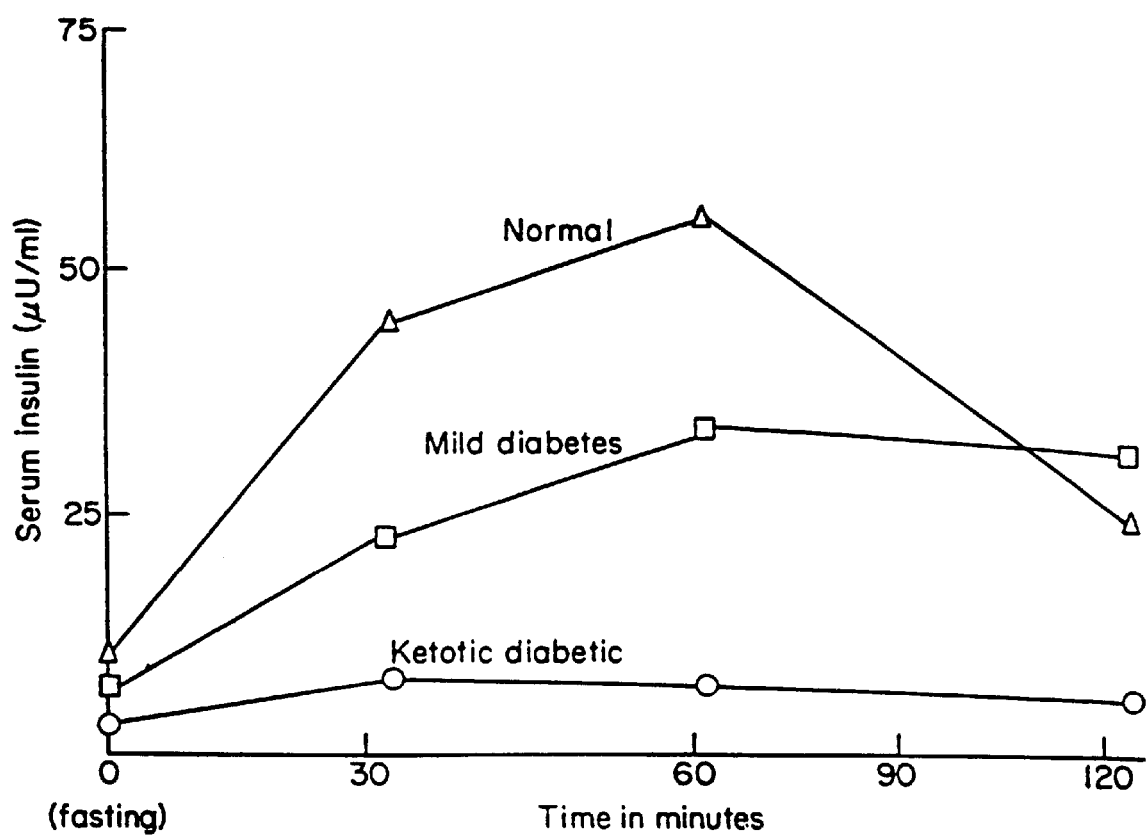
FIG. 1 is a plot showing insulin levels ($\mu$U/mL) over time (minutes) for normal individuals and diabetics.

It is well known that a wide range of biological functions are mediated by the formation of noncovalent, macromolecular complexes. Examples include enzyme-substrate binding, antigen-antibody interactions, leukocyte-endothelial cell adhesion events, drug-receptor binding, and protein-protein interactions. However, utilization of macromolecular complexes as drug delivery systems is relatively new and uninvestigated.

The present application discloses a novel drug delivery system which utilizes a PAL containing a liposome and a naturally occurring or synthetic anionic polymer. The PAL is useful for the oral, parenteral, sublingual, transdermal, conjunctival, intraocular, intranasal, aural, intrarespiratory, rectal, vaginal, or urethral delivery of therapeutic agents. The therapeutic agent can be, for example, but not limited to, genes, peptides, proteins, antibacterials, antifungals, antineoplastics, antiprotozoals, antiarthritics, and antiinflammatory agents. In a preferred embodiment, the therapeutic agent is a gene, a polypeptide, or a protein. In especially preferred embodiments, the therapeutic agent is insulin.

As will be discussed in detail hereafter, the physicochemical properties of the present PALs were investigated. The interactions of liposomes with anionic polymers were monitored using particle size analysis, and by zeta potentials. The physical evidence confirmed the presence of a PAL, wherein an anionic polymer is electrostatically associated, i.e., noncovalently complexed, with a liposome. In accordance with an important feature of the present invention, the anionic polymer is intertwined through the bilayer structure of the liposome, and, accordingly, is present on the external surface of the liposome, the internal surface of the liposome, and within the phospholipid bilayer that forms the liposome. Analysis of an aqueous suspension of a PAL indicated that the physicochemical properties of a PAL are different from a conventional liposome mixture and from a liposome that is surface coated with an anionic polymer. Furthermore, data indicates that PAL formation results from kinetic and thermodynamic equilibria. These studies show that a PAL is well suited for oral delivery of therapeutic agents.

The following discussion is particularly directed to PALs containing a liposome prepared from lecithin and an anionic polymer based on a salt form of polyvinylsulfonic acid or polyvinylphosphonic acid. However, persons skilled in the art are aware that other phospholipids and anionic polymers similarly can be used to provide a PAL of the present invention.

As previously discussed, a drug, like insulin, can treat and control a disease, like diabetes, but cannot prevent, attenuate, or rectify complications associated with the disease, such as vascular problems, like heart disease and "diabetic foot." Therefore, it would be advantageous to administer insulin to a diabetic in a form that not only treats the disease, but also prevents, alleviates, or reverses complications associated with the disease. A composition containing a drug, like insulin, and a PAL provides these advantages.

An important additional advantage would be to provide a method of administering a drug, like insulin, orally. Insulin, and other drugs, and especially genes and many protein and polypeptide-based drugs, cannot be administered orally because the drug is altered in the stomach, and, therefore, is unavailable to the body in a form to combat or control a disease.

With respect to diabetes, it is known that glucose can complex with proteins to produce toxic by-products. Such toxic by-products have been theorized as the cause of the complications associated with diabetes. It also has been observed that diabetics have elevated levels of GAGs in serum and urine, and a lower GAG content in their kidney cell membranes. It also is known that administration of GAGs to diabetic animals inhibited and/or reversed some vascular abnormalities associated with diabetes. Diabetics also have altered blood chemistries, including elevated levels of various enzymes in addition to glucose.

Therefore, the following has been hypothesized, but is not relied upon, as a cause for the complications associated with diabetes. In particular, the interior of vascular walls are lined with endothelial cells. Branching from the endothelial cells are proteoglycan molecules. Glucose is able to bond with these surfaces of the endothelial cells. However, GAGs also are known to be present on the proteoglycan branches on the surface of endothelial cells. In addition, insulin also is known to have the capability to complex with the GAG compounds. It is hypothesized, therefore, that insulin complexes with the GAGs present on the branches of the endothelial cells, and that the GAGs-insulin complexes are removed from the cell by enzymatic activity, thereby leaving the surfaces endothelial cells devoid of GAGs compounds.

An increased insulin dosage provides sufficient insulin to account for the insulin lost as a result of the insulin-GAGs interaction. But the sloughing of GAGs from endothelial cells exposes the vascular surface to numerous unwanted reactions, including repeated glycosylation. Repeated glycosylation can be exacerbated by the naturally elevated levels of serum glucose in a diabetic. Therefore, it has been found that the interaction between insulin and the GAGs on the endothelial cells can be circumvented by complexing insulin such that the insulin is unavailable to interact with the GAGs on the surface of endothelial cells.

Since the present investigators have found evidence of a GAGs complex with insulin, the present investigators considered complexing insulin with a GAG, and thereby protect vascular endothelial cells from the harmful effects of constant exposure to insulin. Then, the insulin would not be available to complex with GAGs on the surface of endothelial cells. As a result, the endothelial cells would not be vulnerable to glycosylation as a result of a sloughing off of the GAGs-insulin complex.

However, GAGs are well known anticoagulants and their long term effects on a diabetic are unknown. As a result, a GAG could not be administered to an individual on a long term basis because, for example, the blood of the individuals would be thinned too greatly.

In accordance with the present invention, insulin, and other drugs, can be administered with a suitable PAL to provide a drug delivery system that avoids the interaction between insulin and a GAG on the surface of an endothelial cell. It is hypothesized that the vascular endothelial cells therefore are spared from undesirable reactions, like glycosylation, and vascular complications associated with diabetes can be eliminated or attenuated. Furthermore, the present PALs make the insulin available to the individual, such that diabetes is controlled. Similarly, other drugs, in addition to insulin, can be administered in conjunction with a PAL, and are available to treat the disease of concern.

The use of a PAL containing a suitable naturally occurring or synthetic anionic polymer as a drug delivery system also avoids the harmful side effects of GAGs (e.g., anticoagulation), and insures the quality, reproducibility, and uniformity of the drug delivery system because the anionic polymers have a reproducible chemical makeup, and the molecular weight can be controlled. Furthermore, by a proper selection of an anionic polymer, the in vivo behavior of insulin can be controlled to optimize the pharmacologic response of insulin, and the route of administration can be regulated. The proper selection of an anionic polymer also provides a drug delivery system that is site specific because different anionic polymers have an affinity to different specific cell surfaces.

A drug administered with a PAL can be essentially any drug or therapeutic agent. The drug can be a naturally occurring or synthetic drug. The drug can be monomeric, or oligomeric or polymeric, like a gene, a polypeptide, or a protein. In addition, the drug can be water soluble or water insoluble, or a mixture thereof. Water-soluble drugs are microencapsulated by the PAL. Water-insoluble drugs reside in the hydrophobic bilayer of the liposome of the PAL. Preferred drugs are polypeptide or protein based.

Preferably, the drug has at least one positively charged site. The positively charged site usually is a quaternary ammonium nitrogen atom. If the drug is a synthetic drug, the drug often contains a nitrogen atom that can be quaternized.

If the drug is a naturally occurring drug, the drug often contains an amino acid having a positively charged site. These quaternized nitrogen atoms and positively charged sites are available to complex with the neutralized acid moieties of the anionic polymer.

Other drugs that can be administered with a PAL of the present invention include, but are not limited to, genes; antiinflammatory drugs, like tereofenamate, proglumetacin, tiaramide, apazone, benzpiperylon, pipebuzone, ramifenazone, and methotrexate; antiinfective drugs, like isoniazid, polymyxin, bacitracin, tuberactionomycin, and ethryomycin; antiarthritis drugs, like penicillamine, chloroquine phosphate, glucosamine, and hydroxychloroquine; diabetes drugs, like insulin, and glucagon; and anticancer drugs, like cyclophosphamide, interferon a, interferon β, interferon γ, vincristine, and vinblastine.

A PAL is prepared from a liposome and an anionic polymer having a plurality of acid moieties in a salt form. The anionic polymer in the salt form, therefore, has a plurality of negative charges. The liposome is prepared from a phospholipid.

A liposome is a membrane vesicle prepared from a phospholipid. Structurally, a liposome is a bilayer spherical membrane having polar ends of phospholipids in one layer forming the external surface of the spherical membrane and the polar ends of phospholipids in a second layer forming the internal surface of the spherical membrane. The nonpolar, hydrophobic tails of the phospholipids in the two layers align to form the interior of the bilayer membrane.

The bilayer liposomes can microencapsulate compounds, and transport the compounds through environments wherein the compound normally is degraded. Liposomes, therefore, have been suggested for use in drug delivery systems.

However, liposomes typically are broken down in the liver, and, therefore, exist in the circulatory system for only a very short time, generally for a period of minutes. Liposomes, therefore, have not served as a good delivery system for drugs because a liposome-drug complex does not survive for a sufficiently long time in the vascular system to reach the target site for the drug.

Liposomes have been modified to avoid rapid clearance in the liver. For example, STEALTH® liposomes, available from Liposome Technologies, remain in the vascular system for about 48 to about 96 hours, and have the ability to deliver drugs. These modified liposomes have polyethylene glycol (PEG) molecules covalently bound to the external surface of the liposome. However, these PEG-modified liposomes are difficult and expensive to manufacture.

A second type of modified liposome is a conventional liposome coated with a polymer. A polymer-coated liposome is prepared by simply adding a polymer to an aqueous dispersion of a liposome. The polymer is merely coated on the exterior surface of the liposome. However, when the coated liposome is diluted in water or saline, the polymer and liposome dissociate to regenerate a conventional liposome and the polymer. As illustrated in detail hereafter, the present PALs, containing an anionic polymer that is electrostatically, i.e., not covalently, bound to a liposome, do not dissociate to a liposome and an anionic polymer upon water dilution.

The first step in the preparation of a PAL is formation of a conventional liposome from phospholipids. The phospholipids used to form a liposome useful in the present invention are not limited. The liposome, therefore, can be prepared by conventional techniques from phosphatidylethanolamine (i.e., cephalin), phosphatidylcholine (i.e., lecithin), phosphatidylserine, phosphatidylinositol, phostidylglycerol, 3'-O-lysylphosphatidylglycerol, cardiolipin, sphingomyelin, and mixtures thereof, for example. In general, the phospholipid can be any glyceride esterified by $C_6$–$C_{24}$ fatty acids at the 1,2-positions and having a phosphoric acid ester residue at the 3-position.

Preferred phospholipids have a phosphoric acid ester residue containing a positive charge, typically a quaternary ammonium nitrogen. Such preferred phospholipids include, but are not limited to phosphatidylethanolamine, phosphatidylcholine, phosphatidylserine, and 3'-O-lysylphosphatidylglycerol. The positive charge on the preferred phospholipids permits an increased electrostatic binding between the liposome and the negatively charged sites on an anionic polymer.

In accordance with an important feature of the present invention, it is not necessary to use a purified phospholipid to form the liposome. Commercial phospholipids, like commercial lecithin, can be used in the present invention, and, therefore, provide economies in providing a PAL of the present invention. Surprisingly, it also has been found that a crude commercial phospholipid, which contains a mixture of phospholipids, can provide a PAL having greater efficacy than a PAL prepared from a purified phospholipid.

An anionic polymer used to prepare a PAL has a plurality of acid moieties. Any physiologically acceptable anionic polymer can be used as long as the anionic polymer contains sufficient acid moieties in the salt form to complex with the liposome. The anionic polymer is prepared by adding a base to an aqueous solution in the polymer. The base typically is an alkali metal hydroxide, like sodium hydroxide or potassium hydroxide. However, other physiologically acceptable alkalis can be used to neutralize the polymer. The acid moieties are present substantially, i.e., 30% or greater, in a salt form. Preferably, at least 50% of the acid moieties are present in the salt form. To achieve the full advantage of the present invention, at least 70% of the acid moieties are present in the salt form.

Typically, the anionic polymer has sufficient acid moieties if the polymer can be solubilized in water by neutralizing the polymer with a base. Such polymers are prepared from a monomer, or mixture of monomers, wherein at least 25% of the monomers, by weight of the polymer, contain an acid moiety. Preferably, at least 40% of the monomers, by weight of the polymer, contain an acid moiety. To achieve the full advantage of the present invention, at least 60% of the monomers, by weight of the polymer, contain an acid moiety. If the polymer is a homopolymer, the monomers containing an acid moiety can be 100% by weight of the polymer. By proper selection of the anionic polymer, persons skilled in the art are able to regulate the site-specific delivery of the drug, the pharmacologic response of the drug, and the route of administration of a drug formulated with the PAL.

The anionic polymer can be a synthetic polymer or a naturally occurring polymer. In general, the anionic polymer has an $M_W$ of about 1,000 to about 1,000,000 and preferably about 2,000 to about 100,000. To achieve the full advantage of the present invention, the polymer has an $M_W$ of about 6,000 to about 50,000.

With respect to synthetic polymers, preferred anionic polymers are linear polymers. However, lightly cross-linked anionic polymers also can be used. A lightly crosslinked polymer has one to about five crosslinks crosslinking the linear chains of the polymer molecule and is soluble in water. An important feature of the polymer is that the polymer is water soluble, and contains acid moieties, such as carboxyl, phosphate, phosphonate, sulfate, sulfonate, phenolic, or any other moiety having a labile hydrogen that can be removed from the moiety to provide a negatively charged site on the polymer.

The anionic polymer typically is an acrylic polymer containing a sufficient amount of acid-containing monomers, like acrylic acid, methacrylic acid, vinylsulfonic acid, or vinylphosphonic acid. The acid-containing monomer can be, but is not limited to, acrylic acid, methacrylic acid, maleic acid, fumaric acid, itaconic acid, mesaconic acid, citraconic acid, vinylsulfonic acid, vinylphosphonic acid, and similar α, β-unsaturated carboxylic acids and α, β-unsaturated dicarboxylic acids. The polymer is in a salt form when utilized to prepare a PAL.

The anionic polymer can be a homopolymer of an acid-containing monomers, like α, β-unsaturated carboxylic acids, or can be a copolymer. For example, a suitable copolymer can be an acid-containing monomer that is copolymerized with ethylene, propylene, or a similar $C_4$–$C_5$ alkene, or a $C_1$–$C_{12}$ ester of an α, β-unsaturated carboxylic acid, vinyl propionate, acrylamide, or methacrylamide, or that is copolymerized with an aromatic monomer, like styrene, α-methyl toluene, or vinyl toluene. Other comonomers include vinylpyrrolidone, vinyl alcohol, vinyl acetate, and vinyl alkyl ethers.

Examples of anionic polymers include, but are not limited to, polyacrylic acid, polyvinylphosphonic acid, polyvinylsulfonic acid, polystyrenesulfonic acid, polymaleic acid, polymethacrylic acid, polyvinylsulfuric acid, poly(2-methacroyloxyethane-1-sulfonic acid, poly(4-vinylbenzoic acid), poly(3-(vinyloxy)propane-1-sulfonicacid), poly(3-(vinyloxy)-propane-1-sulfonic acid), poly(3-methacryloxypropane-1-sulfonic acid), polymethacrylic acid, poly(4-vinylphenol), poly (4-vinylphenyl sulfuric acid), and poly(N-vinylsuccinamidic acid). In other embodiments, an anionic polymer containing an aromatic monomer can be sulfonated or sulfated to position acid groups on the aromatic monomer. Preferred anionic polymers are salt forms of polyacrylic acid, polyvinylsulfonic acid, and polyvinylphosphonic acid.

With respect to naturally occurring anionic polymers, the above-discussed disadvantages resulting from using a GAG limits the naturally occurring polymers to those that do not adversely effect an individual over the long term, i.e., a strong anticoagulant should not be used as the polymer. However, GAGs that act as anticoagulants have a relatively high molecular weight of about 12,000 or greater. Therefore, analogs of GAGs that do not act as strong anticoagulants can be used as the polymer. Such polymers have a structure that is similar to a GAG compound, but have a lower $M_W$, i.e., less than about 12,000.

Therefore, useful naturally occurring anionic polymers have an $M_W$ of about 1,000 to about 12,000, and preferably about 2,000 to about 8,000, and do not act as coagulants at the level they are administered in the PAL, i.e., about 2 mg/day. This dose is less than the 20 mg/day dose required to observe anticoagulation effects and, therefore, mild anticoagulants can be used as the polymer. Furthermore, the low $M_W$, naturally occurring polymers have a greater bioavailability. For example, heparin having an $M_W$ of about 6,000 is 85% bioavailable, but as the $M_W$ increases, bioavailability decreases exponentially. Suitable naturally occurring anionic polymers therefore include, but are not limited to, heparin, dermatan sulfate, chondroitin sulfate, keratan sulfate, heparan sulfate, hyaluronic acid, the various forms of carrageenan, and mixtures thereof, having a molecular weight ($M_W$) of about 1,000 to about 12,000. Overall, a synthetic anionic polymer is preferred over a naturally occurring anionic polymer because synthetic polymers are more uniform chemically, and a desired $M_W$ is more easily achieved.

A PAL of the present invention, therefore, is a novel drug delivery system containing a synthetic or a natural anionic polymer electrostatically complexed with a liposome. In general, a PAL is manufactured by first preparing a conventional liposome from phospholipids by techniques known in the art. Then a liposome/polymer complex is formed by incubating the liposome with an anionic polymer in an aqueous medium. During this step, the anionic polymer electrostatically binds to the exterior surface of the liposome. The liposome/polymer complex is isolated, then solubilized in an organic solvent and dried. The PAL is formed by adding an aqueous medium to the dried liposome/polymer complex. It should be noted that a PAL is formed only when an anionic polymer is incubated with a liposome. The addition of an anionic polymer to a phospholipid prior to formation of a liposome does not result in a PAL.

The organic solvent used to solubilize the liposome/polymer complex is a nonpolar solvent, preferably having a low boiling point. Useful organic solvents include hydrocarbons and chlorinated hydrocarbons, like pentane, heptane, benzene, toluene, chloroform, carbon tetrachloride, methylene chloride, trichloroethane, and perchloroethylene, for example.

As illustrated in detail hereafter, a PAL is substantially different from the liposome/polymer complex. The liposome/polymer complex is a liposome having its exterior surface coated with a polymer. This complex dissociates when dissolved in aqueous media. In contrast, a PAL does not dissociate in water. It is theorized that, during hydration of the dried liposome/polymer complex to form a PAL, the polymer no longer merely coats the exterior surface of the liposome, but is intertwined throughout the two layers of the liposome. Accordingly, a portion of the polymer is electrostatically bound to the external surface of the liposome, and a portion of the polymer is electrostatically bound to the internal surface of the liposome. In addition, the polymer chain extends from the external surface, through the two layers of the liposome, to the internal surface of the liposome. The PAL structure, therefore, is analogous to a thread of anionic polymer that is repeatedly strung to and from the external surface of the liposome, through the phospholipid bilayer, and to and from the internal surface of the liposome. The polymer, therefore, is unable to dissociate from the liposome when the PAL is diluted in water.

The following example illustrates the preparation of a PAL of the present invention.

EXAMPLE

Conventional liposomes were prepared according to the film cast method by placing about 150 mg (milligrams) of egg yolk lecithin (available from Sigma Chemical Co., St. Louis, Mo.) in a 50 mL (milliliter) round-bottomed flask, then dissolving the lecithin in 20 mL of chloroform. The chloroform was evaporated from the lecithin solution using a rotary evaporator, leaving a dried film of lecithin on the bottom of the flask. Then, 10 mL of pure water was added to the flask, and the resulting suspension was sonicated in a bath sonicator for about 5–7 minutes to provide conventional lecithin liposomes.

Next, about 10 mL of an aqueous solution containing 5 mg/mL of polyvinylsulfonic acid was added to 10 mL of the lecithin liposome suspension containing 15 mg/mL of the liposome to form a liposome/polymer complex. The resulting suspension was mixed on a magnetic stirrer, under a constant flow of nitrogen, for an incubation time of about 1 to about 96 hours at about 25° C. Water then was removed from the suspension by rotary evaporation, and the liposome/polymer complex was dried to form a film. Next, about 10 mL of chloroform was added to the liposome/polymer complex to dissolve the liposome/polymer complex. The resulting solution was filtered through a 5 $\mu$M syringe filter to remove uncomplexed polyvinylsulfonic acid that precipitated from the solution. The chloroform filtrate was evaporated by rotary evaporation, and the liposome/polymer complex was dried to a film under nitrogen. The PAL was prepared by hydrating the liposome/polymer complex film with about 10 mL of pure water, and bath sonicating the resulting suspension for about 5 minutes. The PALS, having a diameter of about 10 microns, were reduced in size to about 5 microns, by extruding the suspension through a 100 nm polycarbonate filter. The size-reduction step provides a PAL of sufficiently small size (e.g., about 0.1 to about 5 microns) to pass through the vascular system. The PALs also can be reduced in size by sonication. In addition, if desired, an aqueous isotonic buffer solution, rather than pure water, can be used to hydrate the liposome/polymer complex and form a PAL. The isotonic buffer solution has a pH of 7.4, and contains 10 mM HEPES buffer, 140 mM sodium chloride, and 10 mM potassium chloride.

The PAL prepared in the above example can be formulated with a water-soluble drug, a water-insoluble drug, or a mixture thereof. A water-soluble drug is encapsulated by the PAL, whereas a water-insoluble drug is positioned in the hydrophobic bilayer of the PAL. A present PAL also provides negatively charged sites on the anionic polymer chain to electrostatically bind a drug having a positive charge. As illustrated hereafter, the PAL remains intact in the vascular system for up to several hours, thereby allowing the drug to reach its target site. The PAL also is capable of releasing the drug such that the drug can perform its intended function.

Studies were performed to elucidate the structure of a PAL. In one experiment, a test was performed to determine if the anionic polymer could be detected in an aqueous dispersion of the PAL of the above Example. In this test, an aqueous suspension of the lecithin-polyvinylsulfonic acid PAL of the above example was prepared, and an aqueous solution of polyvinylsulfonic acid was prepared in a separate vessel. Each mixture was evaporated to dryness, and a volume of chloroform then was added to each residue. The chloroform solutions were filtered through 5 $\mu$m syringe filters and the filtrates were evaporated to dryness. A known volume of water was added to each residue and the resulting aqueous solutions analyzed for the presence of polyvinylsulfonic acid. The presence of a polymer was not found in the aqueous solution derived from polyvinylsulfonic acid. The polyvinylsulfonic acid was precipitated by the chloroform. In contrast, polyvinylsulfonic acid was detected in the solution derived from the PAL. This test showed that anionic polymers can interact with liposomes to form noncovalent, chloroform soluble, PALs.

Another test was performed to determine the relationship between the weight of anionic polymer added to the liposome and the weight of anionic polymer in the PAL. In this test, about 40 mL of a solution of conventional liposomes containing 15 mg/mL phospholipids was prepared as described in the above Example, and divided into four equal portions. Individual polyvinylsulfonic acid solutions containing 0.12, 1.2, 6.2, and 12.5 mg of polymer, respectively, were added to individual portions of the liposome, and each resulting solution was processed to form a PAL. The PAL was extracted into chloroform and analyzed for amount of anionic polymer.

Figure 2:
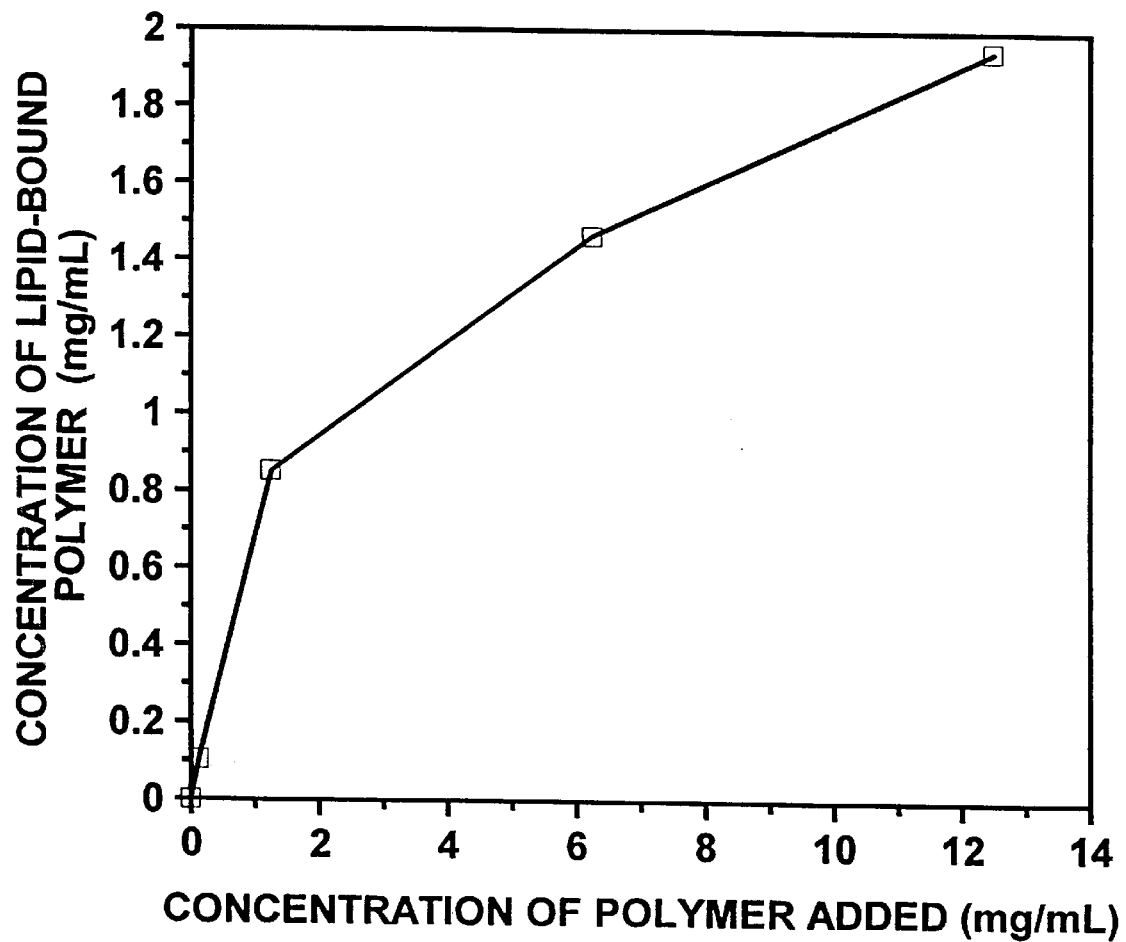
FIG. 2 is a plot of lipid-bound polymer concentration (mg/mL) vs. concentration of polymer (mg/mL) added to a liposome.

Each PAL was analyzed for the presence of polymer by a standard azure dye-binding assay. The results are summarized in FIG. 2. For each data point in FIG. 2, the liposomes were incubated with the polymer for 48 hours at room temperature. FIG. 2 shows that the concentration of a PAL increases as the amount of anionic polymer allowed to incubate with the liposome increase, as dictated by the kinetic binding constant for the particular liposome and polymer.

Therefore, to achieve a PAL containing about 5% to about 20% by weight of an anionic polymer, the weight ratio of anionic polymer to liposome used in the preparation of a PAL is at least about 2:1, and preferably at least about 5:1. To achieve the full advantage of the present invention, the weight ratio of anionic polymer to liposome is at least about 10:1. Any excess, uncomplexed anionic polymer is removed when the liposome/polymer complex is dissolved in an organic solvent. The complex is soluble in the organic solvent, whereas the anionic polymer precipitates from the solvent, thereby allowing a facile separation by filtration. The data in FIG. 2 confirm that an anionic polymer is present in a PAL, and that the total amount of anionic polymer in the PAL is related to the initial concentration of anionic polymer incubated with the liposome.

Figure 3:
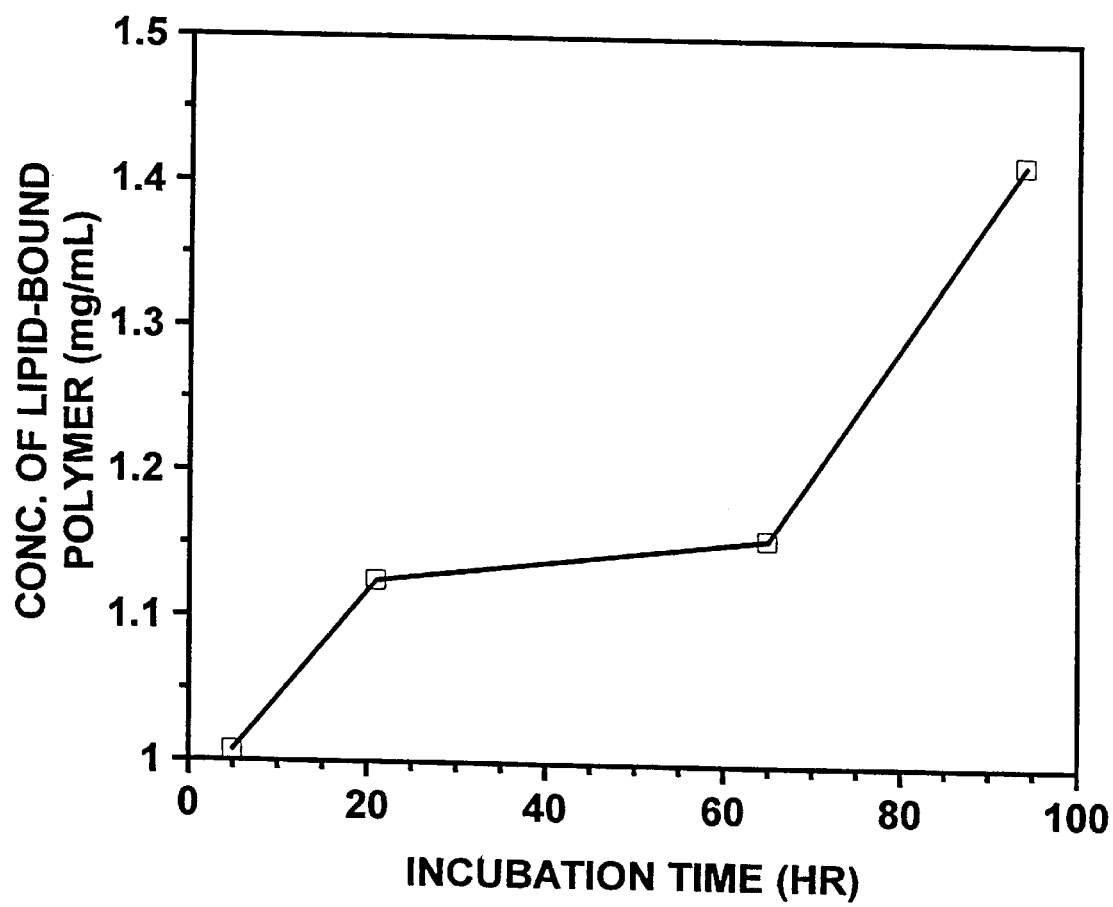
FIG. 3 is a plot of lipid-bound polymer concentration (mg/mL) vs. incubation time (hrs.)

Another test examined the effect of incubation time on formation of the lipid/polymer complex. In this test, a stock solution containing 15 mg/mL conventional liposomes was incubated with polyvinylsulfonic acid for 96 hours. Aliquots were removed from the mixture periodically, then processed into PALs. The PALs were analyzed for anionic polymer content. The results are summarized in FIG. 3. The data in FIG. 3 indicate that the amount of anionic polymer in a PAL increases as incubation time increases, thereby showing that the lipid/polymer complex is a thermodynamically favored species.

The above experiments show that the amount of anionic polymer in a PAL can be adjusted to a desired level by judiciously selecting the phospholipid and anionic polymer, by judiciously selecting the amount of anionic polymer added to the liposome, and by varying the incubation time. Useful PALs contain about 2% to about 30%, and preferably about 5% to about 20%, by weight of an anionic polymer.

The particle size and zeta potential (i.e., charge on the liposome) of conventional liposomes, polymer-coated liposomes, and PALs, also were determined. As described above, polymer-coated liposomes consist of a simple mixture of conventional liposomes and an anionic polymer, like polyvinylsulfonic acid. A comparison among the three liposome forms is summarized in Tables 1 and 2.

TABLE 1

| Particle Size Analysis of Various Liposomes | |
|---|---|
| Liposome Type | Diameter (nm)[1] |
| Conventional | 131.9 ± 35.5 |
| PAL | 120.1 ± 37.8 |
| Polymer coated | 138.9 ± 45.1 |

[1]All size determinations were performed using a Nicomp Model 270 Submicron Particle Sizer.

TABLE 2

Comparison of Zeta Potentials of Various Liposomes

| Liposome Type | Zeta Potential (mV)[2] |
|---|---|
| Conventional | −28.7 ± 1.4 |
| Polymer coated | −35.0 ± 1.3 |
| PAL | −50.8 ± 1.3 |

[2] All zeta potentials were measured using a Pen Kem Lazer Zee Meter Model 501.

The particle size analysis shows that the PALs are the smallest of the three liposome types. The small PAL particle size suggests that the processing conditions used to prepare the conventional and polymer-coated liposomes have no effect on particle size. However, the small size of a PAL is consistent with the anionic polymer in a PAL threading in and out of the liposome shell, thereby making the PAL smaller in size compared to the two other liposome forms.

A comparison of the zeta potentials for the three forms of liposomes strongly indicates that the surface charge of a PAL is significantly different from the surface charge of the other two liposome forms. The polymer-coated liposomes are only slightly more negatively charged than the conventional liposomes, where the PALs are more than 50% more negatively charged than the coated liposomes. This data suggests that the PALs are fundamentally different from both conventional and polymer-coated liposomes, and have a greater ability to bind to drugs, particularly drugs having a positive charge.

As previously stated, conventional liposomes and polymer-coated liposomes are broken down in the liver within minutes, and, therefore, are unable to effectively deliver a drug to a target site. Such liposomes also are unable to direct a drug to a specific target site. However, a PAL is not broken down in liver quickly, but exists for several hours in the vascular system. Therefore, a PAL is an excellent delivery system to deliver a drug to a target site. In addition, a PAL can be designed to direct a drug to a specific target site. The PALs also have an ability to release the drug so that the drug can perform its intended function.

To illustrate that PALs remain the vascular system for extended time periods, the lecithin-polyvinylsulfonic acid PAL of the Example was admixed with a fluorescent tag and the resulting composition was administered to rabbits by injection. As a comparison, conventional liposome was administered to different rabbits. At various time intervals, a blood sample was taken from the rabbits and the blood was assayed for relative fluorescent intensity. The data is summarized in FIG. 4, which contains a pharmokinetic profile showing that a PAL, in vivo, exists in a circulatory system for a much longer time than a conventional liposome. For example, about 75% of a conventional liposome was consumed one hour after injection, whereas only about 50% of a PAL was consumed one hour after injection. It also was observed that about 20% of the PAL remained in the circulatory system about 6 hours after in vivo injection.

Figure 4:
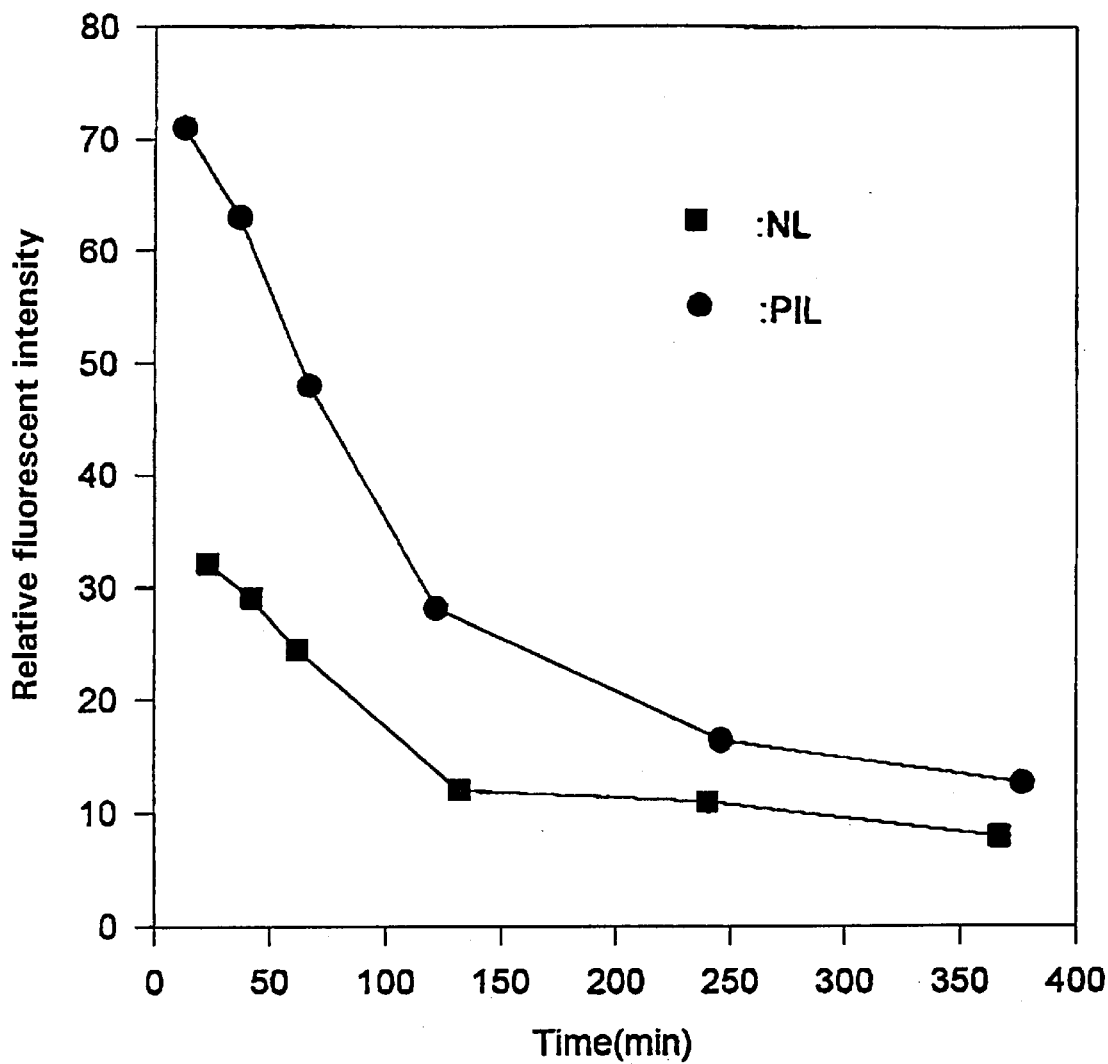
FIG. 4 is a plot of relative fluorescent intensity vs. time (min.).

The results summarized in FIG. 4 show both the stability of a PAL and the effectiveness of a PAL as a drug delivery system. FIG. 4 shows that the PALs remain intact for a relatively extended time period, and do not dissociate immediately after intravenous in vivo administration. Therefore, in addition to demonstrating that a PAL can be formed, it also was demonstrated that a PAL is stable in the vascular system in vivo. The data also shows that a PAL has the ability to release a drug in vivo to treat a disease.

In particular, an aqueous drug composition containing a drug and a PAL can be formed by admixing the drug and a PAL. Such aqueous compositions can be administered by injection or orally. Another important embodiment of the present invention is a solid drug composition containing a drug and a PAL, in a lyophilized form, that can be used to administer the drug orally. In this embodiment, an aqueous drug composition is formed, and the liquid composition then is lyophilized by conventional techniques.

The present invention, therefore, discloses a novel drug delivery system for the oral, parenteral, sublingual, transdermal, conjunctival, intraocular, intranasal, aural, intrarespiratory, rectal, vaginal, or urethral delivery of therapeutic agents. The drug delivery system comprises a PAL, which contains a liposome and a salt form of a polymer having a plurality of acid moieties. The therapeutic agent can be, but is not limited to, genes, peptides, proteins, antibacterials, antifungals, antineoplastics, antiprotozoals, antiarthritics, and antiinflammatory agents. The polymers can be naturally occurring or synthetic, and are commercially available or can be readily synthesized.

The specific physicochemical properties of the PAL can be adjusted by a judicious selection of the phospholipid used to form the liposome, the polymer, the $M_W$ of the polymer, and the number and type of anionic moieties on the polymer, by the weight ratio of liposome to polymer in the PAL, and by the incubation time. The proper selection of a PAL also permits the delivery of a drug to a particular target site. By selecting anionic polymer that has an affinity to the specific cell surface at the target site of interest, the drug delivery system can more effectively deliver a drug or therapeutic agent to the target site to act against the disease of concern.

Many modifications and variations of the invention as hereinbefore set forth can be made without departing from the spirit and scope thereof, and only such limitations should be imposed as are indicated by the appended claims.

What is claimed is:

1. A method of manufacturing a polymer-associated liposome comprising a liposome and an anionic polymer, wherein the anionic polymer is electrostatically complexed with the liposome, said method comprising the steps of:

(a) forming a liposome from a phospholipid in an aqueous medium, wherein the phospholipid is selected from the group consisting of phosphatidylethanolamine, lecithin, phosphatidylserine, phosphatidylinositol, phostidylglycerol, 3'-O-lysylphosphatidylglycerol, cardiolipin, sphingomyelin, and mixtures thereof, (b) adding an anionic polymer to the liposome in the aqueous medium and allowing the liposome and anionic polymer to incubate for a sufficient time to form a liposome/polymer mixture containing a liposome/polymer complex and uncomplexed anionic polymer, wherein the anionic polymer is selected from the group consisting of (i) a naturally occurring polymer having a weight average molecular weight of about 1,000 to about 12,000, and selected from the group consisting of heparin, dermatan sulfate, chondroitin sulfate, keratan sulfate, heparin sulfate, hyaluronic acid, carrageenan, and mixtures thereof (ii) a synthetic polymer selected from the group consisting of a homopolymer of an α, β-unsaturated carboxylic acid, a copolymer of an α, β-unsaturated carboxylic acid and a comonomer, and mixtures thereof, (iii) a salt form of a polymer selected from the group consisting of polyacrylic acid, polyvinylphosphonic acid, polyvinylsulfonic acid, polystyrenesulfonic acid, polymaleic acid, polymethacrylic acid, polyvinylsulfuric acid, poly(2-methacroyloxyethane-1-sulfonic acid, poly(4-vinylbenzoic acid), poly(3-(vinyl-oxy)propane-1-sulfonic acid), poly(3-(vinyloxy)propane-1-sulfonic acid), poly(3-methacryloxypropane-1-sulfonic acid), polymethacrylic acid, poly(4-vinylphenol), poly(4-vinylphenyl sulfuric acid), poly(N-vinylsuccinamidic acid), and mixture thereof, (c) removing the aqueous medium from the liposome/polymer mixture, (d) adding an organic solvent to the liposome/polymer mixture to solubilized the liposome/polymer complex and precipitate the uncomplexed anionic polymer, (e) separating the complexed anionic polymer from the organic solvent and the solubilized liposome/polymer complex, (f) separating the liposome/polymer complex from the organic solvent, and (g) adding water to the liposome/polymer complex to form the polymer-associated liposome.

2. The method of claim 1 wherein the anionic polymer of the polymer-associated liposome is present on an external surface of the liposome, on an internal surface of the liposome, and extends through a phospholipid bilayer of the liposome.

3. The method of claim 1 wherein the phospholipid has a positive charge.

4. The method of claim 3 wherein the phospholipid is selected from the group consisting of phosphatidylethanolamine, phosphatidylcholine, phosphatidylserine, 3'-O-lysylphosphatidylglycerol, and mixtures thereof.

5. The method of claim 1 wherein the weight ratio of the anionic polymer to the liposome during incubation is at least about 2 to 1.

6. The method of claim 1 wherein the weight ratio of the anionic polymer to the liposome during incubation is at least about 5 to 1.

7. The method of claim 1 wherein the weight ratio of the anionic polymer to the liposome during incubation is at least about 2 to 1 to about 10 to 1.

8. The method of claim 1 wherein the liposome and anionic polymer are incubated for a sufficient time to form a liposome/polymer complex containing about 2% to about 30% by weight of the anionic polymer.

9. The method of claim 1 wherein the liposome and anionic polymer are incubated for about 1 to about 96 hours at 25° C.

10. The method of claim 1 wherein the anionic polymer of (b) (ii) and (b) (iii) has a plurality of acid moieties, wherein at least 30% of the acid moieties are in a salt form, and has a weight average molecular weight of about 1,000 to about 1,000,000.

11. The method of claim 10 wherein at least 50% of the acid moieties are in the salt form.

12. The method of claim 10 wherein the polymer comprises about 25% to 100%, by weight of the polymer, of a monomer having an acid moiety.

13. The method of claim 10 wherein the polymer has a weight average molecular weight of about 6,000 to about 50,000.

14. The method of claim 1 wherein the anionic polymer is crosslinked.

15. The method of claim 1 wherein the comonomer of (b) (ii) is selected from the group consisting of ethylene, propylene, a $C_{4-5}$alkene, a $C_1$–$C_{12}$ ester of an α, β-unsaturated carboxylic acid ester vinyl propionate, acrylamide, methacrylamide, styrene α-methyl toluene, vinyl toluene, vinylpyrrolidone, vinyl alcohol, vinyl acetate, a vinyl alkyl other and mixtures thereof.

16. The method of claim 1 wherein the synthetic of (b) (ii) polymer comprises an α, β-unsaturated carboxylic acid selected from the group consisting of acrylic acid, methacrylic acid, maleic acid, fumaric acid, itaconic acid, mesaconic acid, citraconic acid, vinylphosphonic acid, and mixtures thereof.

17. the method of claim 1 wherein the synthetic polymer of (b) (ii) comprises sulfated aromatic monomers or sulfonated aromatic monomers.

18. The method of claim 1 wherein the anionic polymer of (b) (ii) is selected from the group consisting of polyvinylsulfonic acid, polyvinylphosphonic acid, polyacrylic acid, and mixtures thereof.

19. The complex of claim 1 wherein the organic solvent is a nonpolar organic solvent.

20. The complex of claim 1 wherein the organic solvent comprises a hydrocarbon, a chlorinated hydrocarbon, or a mixture thereof.

21. The complex of claim 1 wherein the water used to form the polymer-associated liposome from the liposome/polymer complex further comprises a buffer, sodium chloride, potassium chloride, or a mixture thereof.

22. The complex of claim 1 further comprising the step of reducing the particle size of the polymer-associated liposome of step (g) to about 5 microns or less.

23. A polymer-associated liposome prepared by the method of claim 1.

24. A method of treating a disease and complications associated with the disease comprising administering a therapeutic amount of a drug composition to an individual, said composition comprising:

(a) a drug, and (b) a polymer-associated liposome comprising (i) a liposome comprising a bilayer of a phospholipid wherein the phospholipid is selected from the group consisting of phosphatidylethanolamine, lecithin, phosphatidylserine, phosphatidylinositol, phostidylglycerol, 3'-O-lysylphosphatidylglycerol, cardiolipin, sphingomyelin, and mixtures thereof, and (ii) and anionic polymer wherein the anionic polymer is selected from the group consisting of (A) a naturally occurring polymer having a weight average molecular weight of about 1,000 to about 12,000, and selected from the group consisting of heparin, dermatan, sulfate, chondroitin sulfate, keratan sulfate, heparan sulfate, hyaluronic acid, carrageenan, and mixtures thereof (B) a synthetic polymer selected from the group consisting of a homopolymer of an α, β-unsaturated carboxylic acid, a copolymer of an α, β-unsaturated carboxylic acid and a comonomer, and mixtures thereof, (C) a salt form of a polymer selected from the group consisting of polyacrylic acid polyvinylphosphonic acid, polyvinylsulfonic acid, polystyrenesulfonic acid, polymaleic acid, polymethacrylic acid, polyvinylsulfuric acid, poly(2- methacroyloxyethane-1-sulfonic acid, poly(4-vinylbenzoic acid), poly(3-(vinyloxy)propane-1-sulfonic acid), poly(3-(Vinyloxy)propane-1-sulfonic acid), poly(3-methacryloxypropane-1-sulfonic acid), polymethacrylic acid, poly(4-vinylphenol), poly(4 vinylphenol sulfuric acid), poly(N-vinylsuccinamidic acid), and mixtures thereof, wherein a weight ratio of the liposome to the polymer is about 80:20 to about 95:5, and wherein the anionic polymer of the polymer-associated liposome is present on an external surface of the liposome, on an internal surface of the liposome, and extends through a phospholipid bilayer of the liposome, and wherein the polymer-associated liposome is prepared by the method of claim 1.

25. The method of claim 24 wherein the composition is administered by injection.

26. The method of claim 24 wherein the composition is administered orally.

* * * * *

UNITED STATES PATENT AND TRADEMARK OFFICE
CERTIFICATE OF CORRECTION

PATENT NO. : 5,935,599
DATED : August 10, 1999
INVENTOR(S) : Eric J. Dadey

It is certified that error appears in the above-identified patent and that said Letters Patent is hereby corrected as shown below:

Column 16, line 6, "ester" should be --ester,--

Column 16, line 9, "other" should be --ether,--

Column 17, line 3, "poly(3-(Vinyloxy)..." should be --poly(3-(vinyloxy)...--

Column 17, line 6, "poly(4 vinylphenol..." should be --poly(4-vinylphenol...--

Signed and Sealed this

Eighth Day of August, 2000

Attest:

Q. TODD DICKINSON

Attesting Officer

Director of Patents and Trademarks